United States Patent
Wu

(10) Patent No.: US 10,289,377 B2
(45) Date of Patent: May 14, 2019

(54) METHOD AND APPARATUS FOR AUSCULTATING INAUDIBLE SIGNALS

(71) Applicant: Wei Wu, Wenzhou (CN)

(72) Inventor: Wei Wu, Wenzhou (CN)

( * ) Notice: Subject to any disclaimer, the term of this patent is extended or adjusted under 35 U.S.C. 154(b) by 387 days.

(21) Appl. No.: 15/021,688

(22) PCT Filed: Sep. 7, 2014

(86) PCT No.: PCT/CN2014/086085
§ 371 (c)(1),
(2) Date: Mar. 12, 2016

(87) PCT Pub. No.: WO2015/048927
PCT Pub. Date: Apr. 9, 2015

(65) Prior Publication Data
US 2016/0224312 A1 Aug. 4, 2016

(30) Foreign Application Priority Data
Oct. 6, 2013 (CN) .......................... 2013 1 0465951

(51) Int. Cl.
G06F 3/16 (2006.01)
A61B 7/04 (2006.01)
(Continued)

(52) U.S. Cl.
CPC ............... *G06F 3/165* (2013.01); *A61B 7/04* (2013.01); *G01H 11/06* (2013.01); *G10L 19/008* (2013.01); *H03M 1/001* (2013.01); *H04R 1/46* (2013.01)

(58) Field of Classification Search
None
See application file for complete search history.

(56) References Cited

U.S. PATENT DOCUMENTS 4,220,160 A * 9/1980 Kimball .................. A61B 7/04
381/67
4,792,145 A * 12/1988 Eisenberg ................ A61B 7/04
381/67
(Continued)

FOREIGN PATENT DOCUMENTS

CN 102961164 A 3/2013

*Primary Examiner* — Jason C Olson

(57) ABSTRACT

The prior auscultation technology is only applicable to the sound signals within the audio range and conducted by vibration. Disclosed in the present invention are a method and an apparatus for auscultating inaudible signals, and thus inaudible signals can be mapped into the audible range to form audible signals. The method comprises: obtaining signal data which comprise audible or inaudible signal data; extracting a signal waveform from the signal data; determining a play rate which allows the signal waveform to phonate by means of an audio play apparatus; and performing the auscultation with the signal waveform being played through the audio play apparatus at the play rate, or combining the play rate and the signal waveform to thereby constitute an audio signal, and then playing the audio signal through the audio player so as to achieve auscultation. When the method and apparatus of the present invention are applied, auscultation can be achieved on any physical parameter changes expressed by wave-shaped curve, which promises to extract information which would have been difficult to find within the inaudible signal in the prior art and promote the development of science and technology innovations.

17 Claims, 2 Drawing Sheets

(51) Int. Cl.
*G01H 11/06* (2006.01)
*G10L 19/008* (2013.01)
*H03M 1/00* (2006.01)
*H04R 1/46* (2006.01)

(56) References Cited

U.S. PATENT DOCUMENTS

| | | | | |
|---|---|---|---|---|
| 4,922,917 A * | 5/1990 | Dory | ............ | G01N 29/0609 600/437 |
| 5,003,605 A * | 3/1991 | Phillipps | ............ | A61B 5/04085 381/67 |
| 5,873,065 A * | 2/1999 | Akagiri | ............ | G11B 20/00007 381/2 |
| 6,339,719 B1 * | 1/2002 | Lee | ............ | A61B 7/00 600/511 |
| 6,366,887 B1 * | 4/2002 | Zehner | ............ | G01S 7/539 704/267 |
| 6,440,082 B1 * | 8/2002 | Joo | ............ | A61B 5/0535 600/483 |
| 7,300,405 B2 * | 11/2007 | Guion | ............ | A61B 7/00 181/131 |
| 9,364,184 B2 * | 6/2016 | Figgatt | ............ | A61B 5/04023 |
| 2002/0183642 A1 * | 12/2002 | Murphy | ............ | A61B 5/061 600/532 |
| 2003/0002685 A1 * | 1/2003 | Werblud | ............ | A61B 7/04 381/67 |
| 2004/0260188 A1 * | 12/2004 | Syed | ............ | A61B 5/0456 600/509 |
| 2009/0290719 A1 * | 11/2009 | Kugler | ............ | A61B 7/04 381/67 |
| 2011/0276328 A1 * | 11/2011 | Gass | ............ | A61B 5/002 704/235 |
| 2012/0302902 A1 * | 11/2012 | Shin | ............ | A61B 5/02225 600/494 |
| 2013/0197382 A1 * | 8/2013 | Yang | ............ | A61B 7/00 600/528 |
| 2014/0155762 A1 * | 6/2014 | Maskara | ............ | A61B 7/003 600/484 |

* cited by examiner

1 Signal data acquisition unit

2 Signal processing unit

3 Audio play device

METHOD AND APPARATUS FOR AUSCULTATING INAUDIBLE SIGNALS

The present application is based on, and claims priority from, Chinese application number 201310465951.1, filed on 6 Oct. 2013, the disclosure of which is hereby incorporated by reference herein in its entirety.

FIELD OF THE INVENTION

The present invention discloses a method and an apparatus for signal auscultation, especially for auscultating inaudible signals.

BACKGROUND OF THE INVENTION

Sound identification based on auditory is one of the most ancient signal identification methods, and is still wildly used in many fields nowadays. Auscultating the sounds of human heart and lung by means of a stethoscope for medical diagnosis is an application example. This auscultation method has the advantages of simple and easy to apply, therefore, many research organizations and individuals engaged in research and development of auscultation equipment. For example, Chinese patent numbered 2009200623488, "Active noise reduction electronic stethoscope", can actively remove environment noise, to improve the accuracy of stethoscope and the effect of auscultation; for another example, Chinese patent numbered 2011101883094, "A wireless stethoscope", may realize remote auscultation by means of a radio signal transmitting and receiving device. All of these studies, the signal source are limited in the audible frequency range; that is, the signal source is audio signal conducted by vibration with a frequency limited from 20 Hz to 20 KHz, audible by human ear.

However, with the development of science and technology, there is a large number of information in the inaudible or non-sound signals that a human ear cannot hear. For example, the lunar surface topography fluctuation, the yearly precipitation change in a region, the human brain waves fluctuations, the voltage change of an electronic circuit, stock price fluctuations, or the statistical results of a physical phenomenon, etc., that can be recorded and expressed in a format of waveform. Those waveforms either fall outside the frequency range of an audible signal, or are transferring in a way of no-vibration, therefore cannot be heard by human ears and are inaudible signals.

SUMMARY OF THE INVENTION

The purpose of the present invention is to overcome the application limitations of prior signal auscultation method and device, by disclosing a method and an apparatus for auscultating inaudible signals, with which inaudible signals can be mapped into audible range to form audible signals, to extend the sound auscultation recognition applicable range of human from audible signal into inaudible signal, and expand the "scope" of human recognizing the nature.

The prior sound auscultation can be divided into two methods: direct auscultation and indirect auscultation. Direct auscultation means directly auscultating or through a simple mechanical device (such as a medical stethoscope) listening to the sound; indirect auscultation means, first acquiring sound signals with a certain sampling rate and transferring the sound signal into electrical signal or digital signal; then, the electrical signals or digital signals are processed and replayed through an audio player in a play rate equals to the sampling rate. Either way, it is necessary to make sure that 1st, the waveform amplitude change of both listened sound and sound signal should be the same; 2nd, the speed of both listened sound and sound signal should be the same. The working principle of present invention, the method and apparatus for auscultating inaudible signals, is that, suppose an inaudible signal A in which the waveform contains rich information, is inaudible because it travels too fast or too slow beyond the scope of the human ear can feel. If there is an audible signal B, in which the waveform is exactly the same as the waveform of the signal A, traveling in a rate fallen into the scope of the human ear can feel, then, it is possible to auscultate signal A by means of listening signal B. The auscultation method and apparatus of the invention may map inaudible signal A into audible signal B, by means of extracting waveform of signal A then combining with traveling speed of an audible signal to form audible signal B; the mapped signal B will be played through an audio player to realize the auscultation of signal A.

The object of the present invention can be achieved through the following technical scheme. First proposing a method for auscultating inaudible signals:

A method for auscultating inaudible signals, wherein it comprises below steps:

obtaining signal data which comprise audible or inaudible signal data;

extracting a signal waveform from the signal data;

determining a play rate which allows the signal waveform to phonate by means of an audio play apparatus; and performing the auscultation with the signal waveform being played through the audio play apparatus at the play rate, or combining the play rate and the signal waveform to thereby constitute an audio signal, and then playing the audio signal through the audio player.

The method for auscultating inaudible signals, wherein the step of extracting a signal waveform from the signal data, may further comprise:

Normalizing the signal waveform, during the normalizing, the maximum value and minimum value of the signal amplitude can be determined referring the signal itself or other signals, also can be given directly.

The method for auscultating inaudible signals, wherein the play rate which allows the signal waveform to phonate by means of an audio play apparatus, can be any frequency within audio range, or can be a frequency determined by checking the voice output of the audio play apparatus.

The method for auscultating inaudible signals, wherein the step of combining the play rate and the signal waveform to thereby constitute an audio signal, may further comprise:

The audio signal is saved in digital format.

The method for auscultating inaudible signals, wherein the play rate of the audio play device is independent from sampling frequency of signal being auscultated; and the signal data may comprise single or multiple waveform.

To achieve above objective of the invention and realize the method of auscultating inaudible signals, an apparatus for auscultating inaudible signals is proposed here:

An apparatus for auscultating inaudible signals, comprising a signal data acquisition unit 1, a signal processing unit 2 and an audio play device 3, the data obtained by the signal data acquisition unit 1 is processed by the signal processing unit 2 then played by the audio play device 3; wherein the signal processing unit 2 receives signal data from the signal data acquisition unit 1 and extracts the signal waveform from the signal data then combines the waveform with a play rate which allows the signal waveform to phonate by means of the audio play device 3 and is independent from sampling frequency of the signal.

The apparatus for auscultating inaudible signals, wherein the signal processing unit 2 may normalize signal waveform, the maximum value and minimum value of the signal amplitude during the normalization processing can be determined referring the signal itself or other signals, also can be set up directly.

The apparatus for auscultating inaudible signals, wherein the signal processing unit 2 may extract signal waveform from signal data, and combine the signal waveform with a play rate which allows the signal waveform to phonate by means of an audio play apparatus, to thereby constitute an audio signal, and save the audio signal in file format.

The apparatus for auscultating inaudible signals, wherein the signal processing unit 2 may also extract multiple signal waveforms from multiple or a group of data, and combine the signal waveforms with a play rate which allows the signal waveforms to phonate by means of an audio play apparatus, to thereby constitute a multichannel signal, and save the multichannel audio signal in file format.

The apparatus for auscultating inaudible signals, wherein the audio play device 3 comprises a D/A digital/analog converter, changing D/A converting rate of the converter may change play rate of the audio play device 3; and comprises an electric/acoustic conversion unit which converts the electrical signal converted by the D/A converter into sound signal; and may further comprise an audio signal checking unit to test intensity of the audible sound.

The apparatus for auscultating inaudible signals, wherein the signal processing unit 2 may extract signal waveform from signal data, and combine the signal waveform with a play rate which makes the signal waveform inaudible through an audio play apparatus, to thereby constitute an inaudible signal.

There are a variety of normalization formula can be used for signal normalization. In the present invention, the waveform amplitude can be normalized according to the following normalization formula (1), or according to other normalization formulas which make the signal amplitude after normalization meet the requirements of audio player:

$$Y=K(X-X\text{min})/(\text{Max}-\text{Min})-K/2 \tag{1}$$

where,

X is signal waveform before normalization;
Y is signal waveform after normalization;
Xmin is the minimum value of X;
Max is the maximum value of signal;
Min is the minimum value of signal;
K is the variation amplitude of signal after normalization, normally equals to the input signal variation amplitude required by an audio play device.

Advantages

Compared with the prior art, the method and the apparatus of this invention have advantages including:

1. The prior auscultation technology is only applicable to the sound signals within the audio range and conducted by vibration; present invention overcomes these restrictions and can be used for auscultating any signals which can be expressed in format of waveform.

2. Can make full use of general signal data acquisition unit and audio play device, reducing the cost of the invention implementation, and thus is easy to promote;

3. By auscultating inaudible signals, it is hopeful to extract information which would have been difficult to find within the inaudible signal in the prior art and promote the development of science and technology innovations.

Figure 1:
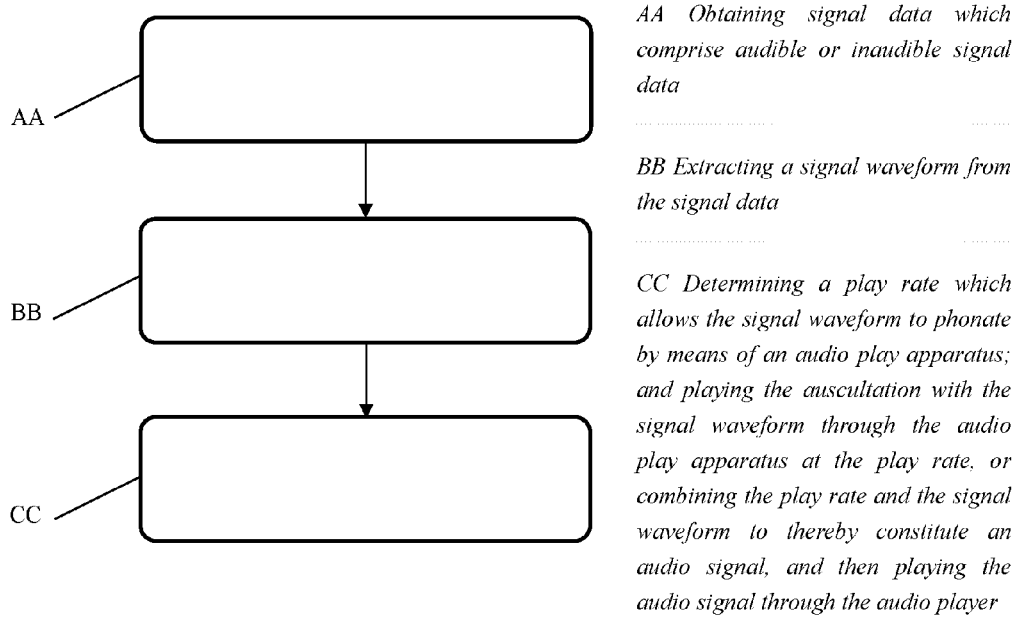
FIG. 1 is a flow chart for the method of the present invention.

Among the figures: signal data acquisition unit 1, signal processing unit 2, audio play device 3, A/D conversion unit 11, USB interface unit 12, network I/O interface unit 13, (Central Processing Unit) 21, memory unit 22, D/A conversion unit 31, electric/acoustic conversion unit 32, audio signal checking unit 33

DESCRIPTION OF THE PREFERRED EMBODIMENT

With reference to the drawings and embodiments the following gives further detailed explanations of present invention. First the preferred embodiment is given below.

FIG. 1 is a flow chart for the method of auscultating inaudible signal presented in this invention. A method for auscultating inaudible signals, wherein it comprises below steps:

1. Obtaining signal data which comprise audible or inaudible signal data;

2. Extracting a signal waveform from the signal data;

3. Determining a play rate which allows the signal waveform to phonate by means of an audio play apparatus; and performing the auscultation with the signal waveform being played through the audio play apparatus at the play rate, or combining the play rate and the signal waveform to thereby constitute an audio signal, and then playing the audio signal through the audio player.

Specific implementation, the signal data can be audible or inaudible signal data, may comprise single or multiple signal waveform; the play rate which allows the signal waveform to phonate by means of an audio play apparatus, can be a frequency within audio range, or can be a frequency determined by checking the voice output of the audio play apparatus.

Figure 2:
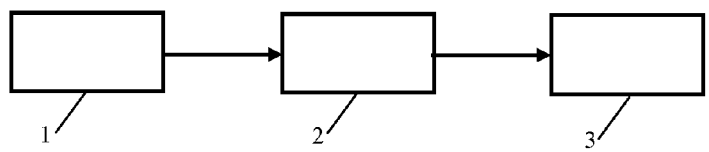
FIG. 2 is a principle diagram of the apparatus of the present invention.

FIG. 2 is a principle diagram of the apparatus of the present invention. As described in FIG. 2, the data acquirement unit 1 may comprise sensor, A/D converter and sampling control circuit, to acquire inaudible signal and convert the signal to electric signal or digital signal; may also comprise various data interfaces such as file or data read device, to directly read measurement results of audible signals from the third party equipment or instrument; or may comprise network interface to receive directly the data transferred from remote. Data processing unit 2 comprises data calculation unit and data story unit, can receive signal data from unit 1 and extract signal waveform from received signal data, and can normalize the received signal into signal with suitable amplitude required by audio play device 3, and combining with suitable play rate, then sending it to audio play device 3 for playing, or save it in audio file format for being played by audio play device; audio play device 3 comprises D/A converter and electric/acoustic conversion unit, can convert the digital signal into analog signal through the D/A convert unit, in a play rate determined by the data processing unit 2, and the analog signal is further converted into the sound and played out by the electric/acoustic conversion unit, the audio play device 3 may further comprise an audio signal checking unit to test if the sound played by the audio play device is correct.

Specifically, the audio play device is an audio signal play device which comprises D/A conversion unit and electric/acoustic conversion unit; and can be a variety of software products or hardware audio play products, and may play all the audio files saved in standard audio file format.

Figure 3:
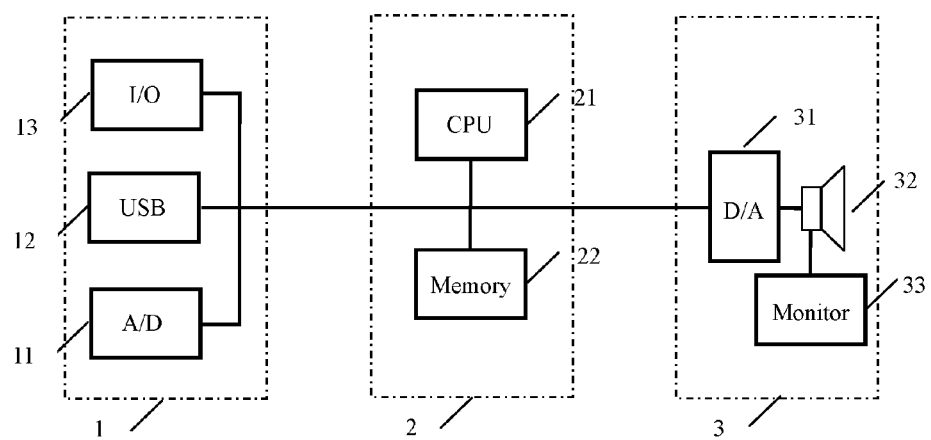
FIG. 3 is a picture for the structure of the embodiments of the invention.
Figure 4:
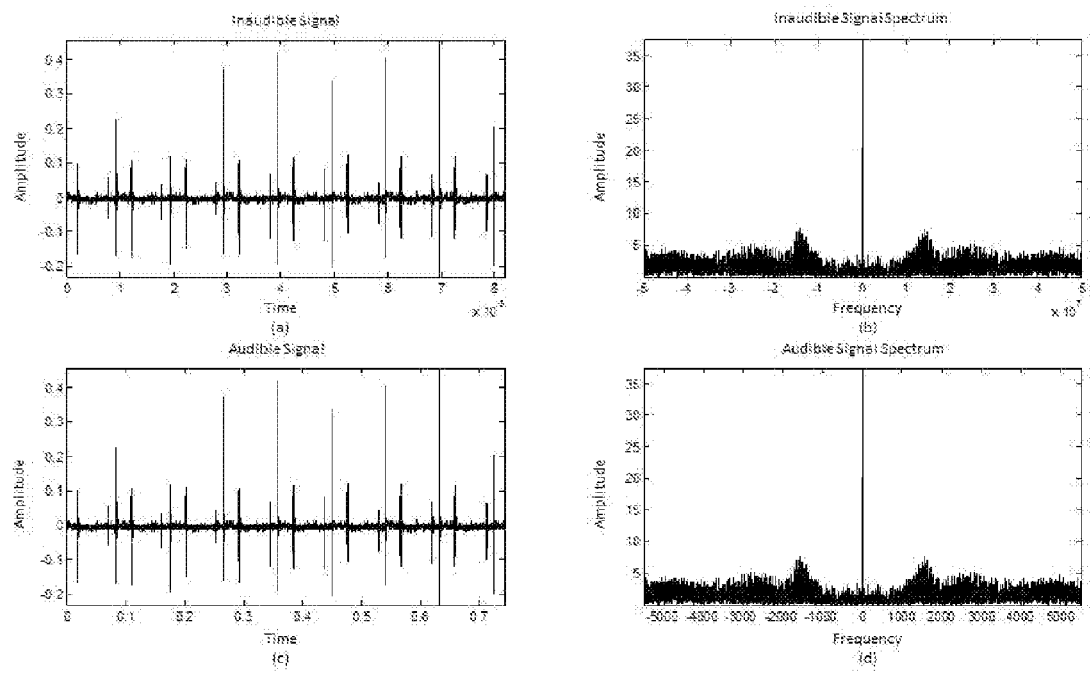
FIG. 4 is a figure of the signals of the embodiment 1.

The following embodiment 1 of the invention combining with FIG. 3 and FIG. 4 further illustrates the work principle of present invention.

Embodiment 1

FIG. 3 and FIG. 4 illustrate the embodiment 1 of the invention. The A/D sampling unit 11 in signal data acquirement unit 1 acquires a voltage signal from a DC/DC converter circuit in a sampling frequency of 100 MHz, and saves the voltage signal at memory unit 22 in signal processing unit 2. The waveform of the acquired voltage signal is illustrated at FIG. 4(*a*). The spectrum of the signal is illustrated at FIG. 4(*b*), showing the main frequency components of the signal is distributed from 2 MHz to 50 MHz while a stronger frequency component is located at 14 MHz; the frequencies of the components are far higher than 20 KHz which is the highest frequency a human ear can sense, so that the signal is inaudible. The acquired signal data includes a variety of parameters such as waveform and sampling rate, etc., the CPU calculation unit 21 in data processing unit 2 extracts the waveform from the signal by means of ignoring parameters other than the waveform, or only copy the waveform data from the signal, then, normalize the waveform. The play rate of the waveform can be set to be a frequency within radio frequency range or be determined by checking the voice output of the audio play device. In this embodiment, the methodology of checking the voice output of the audio play device is used. Specific process is, change the conversion rate of the D/A digital/analog conversion unit 31 to change the play rate of the audio play device, meanwhile listen the sound from audio play device until the play rate reaches 11.025 KHz, that means the signal at FIG. 4(*a*) is mapped to a signal with sampling frequency 11.025 KHz, a clear noise and regular crackling sound is heard; continue the change until the play rate reaches 921 Hz, that means the signal at FIG. 4(*a*) is mapped to a signal with sampling frequency 921 Hz, a sound similar to "bang" sound from a person's heart with background noise can be heard. FIG. 4(*c*) shows a signal mapped from FIG. 4(*a*) with a play rate 11.025 KHz, it is obvious that the waveform remains the same after mapping, but waveform traveling time is changed from 8.192 µS (before mapping) into 0.73 S (after mapping). FIG. 4(*d*) shows the spectrum of the signal after mapping, it is obvious the strong frequency at 14 MHz becomes 1400 Hz after mapping, and the main frequency components of the signal falls into 200 Hz-5500 Hz, the audio range, thus is fully audible. The audio signal obtained after the mapping process is converted into an analog voltage by means of D/A conversion unit 31 which is included in the audio play device 3, and converted to sound by electric/acoustic conversion unit 32. A person skilled in the electric field may adjust the radio play rate of the radio play device, meanwhile listen to the sound from the radio play device, to find out a preferred play rate, and record the duration of the signal being played and, combining with the play rate and signal sampling frequency, evaluate the signal frequency before and after mapping processing, and understand the noise characteristics by auscultating the noise. Auscultating other test points on circuit layout with the same approach, and comparing the auscultation results, may help people understand the electromagnetic interference (EMI) distribution on board.

Embodiment 2

The structure of the embodiment 2 is the same as the structure of the embodiment 1, the difference is, acquiring multiple signal voltage data at multiple test points on circuit board with the same sampling frequency, and saving the acquired signals into memory unit 22, then, the CPU 21 calculating all the acquired signals to find out a signal with maximum amplitude variation, and calculating the maximum and minimum value of the signal, and normalizing all the signals with this maximum value and minimum value according to formula (1), to make the signal which has the maximum waveform variation sound loudly, and other signals with smaller waveform amplitude variation sound weakly, which can recognize different intensity of different signals.

Embodiment 3

The structure of the embodiment 3 is the same as the structure of the embodiment 1, the difference is, the signal processing unit 2 extracts the signal waveform from the signal data then combines the waveform with a play rate which allows the signal waveform to phonate by means of an audio play device, to thereby constitute an audio signal and save the audio signal into memory unit 22 in file format, and the saved audio signal file is further output through I/O network interface or USB interface contained in signal data acquirement unit 1 It is well-know that an audio files saved in format of WAV, MP3, WMA, RA, RM, RMX etc. can be played by a general audio player. In this embodiment we save mapped signals into an audio file in WAV format, by writing the mapped signal's play rate, waveform data length and data resolution (optional 8-bit, 16-bit, or 32-bit; usually 8-bit or 16-bit can meet the requirements of sound identification) into the file header, and the waveform data followed. Considering that an audio play device normally plays the audio file in a play rate equals the sampling frequency of the audio signal, in this embodiment we replace the "sampling frequency" in WAV file heard with Date: Jan. 21, 2019 the play rate of mapped audio file. With the same method we also convert the mapped audio signals into MP3, WMA, RA, RM, RMX format and play them with a general audio play device.

Embodiment 4

The structure of the embodiment 4 is the same as the structure of the embodiment 3, the difference is that the signal processing unit 2 extracts two signal waveforms from two signal data then combines the waveforms with a play rate which allows the signal waveforms to phonate by means of an audio play device, to thereby constitute an multichannel audio signal and save the signal in WAV file format. A user may play the file with a general audio play device, and listen to different signal waveforms by left and right ear with a stereo headphone, to identify the difference between two signals.

Embodiment 5

The structure of the embodiment 5 is the same as the structure of the embodiment 1, the difference is that the audio signal checking unit 33 in audio play device 3, contains a band pass filter unit and an audio voltage detecting unit; the band pass filter unit treats the analog signal from D/A converter, by removing all the frequency components outside the audio range; then the filtered signal is further evaluated the signal intensity by the audio voltage detecting unit, to realize that sound intensity evaluation of a signal played by the audio play device. By listening to the audio signal intensity one may tell if the play rate of the audio play device 3 is set up correctly and well played.

Embodiment 6

The structure of the embodiment 6 is the same as the structure of the embodiment 5, the difference is that the audio signal checking unit 33 in audio play device 3, contains a microphone and an amplifying circuit, which can pick up the sound signal from the audio play device 3 and amplify the signal through the amplification circuit, to realize that sound intensity evaluation of a signal played by the audio play device. By listening to the audio signal intensity one may tell if the play rate of the audio play device 3 is set up correctly and well played.

Embodiment 7

The structure of the embodiment 7 is the same as the structure of the prior embodiments, the difference is that the signal data comprising: 1. The over the years' precipitation fluctuations in a region; 2. the brain wave fluctuations of a person; 3. The exchange rate daily middle price change of the U.S. dollar against the EU Euro in 2007. The data is read through USB interface 12 in signal data acquirement unit 1, then is extracted the waveform by signal processing unit 2, then are normalized according to formula (1) referring itself the amplitude maximum value and minimum value, by changing the play rate of the play device 3 to find out suitable auscultation results, clear waveform sounds from three different type data are listened in play rate 900 Hz, 8000 Hz and 500 Hz respectively.

Embodiment 8

The structure of the embodiment 8 is the same as the structure of the prior embodiments, the difference is, reading a WAV format audio signal file through USB interface 12 in signal data acquirement unit 1, then the signal processing unit 2 extracting signal waveform from the audio signal file, and combine the signal waveform with a play rate which makes the signal waveform inaudible through an audio play apparatus, to thereby constitute an inaudible signal. The specific method is to replace the signal sampling frequency parameters in the WAV file header with the play rate. The WAV file can be played by a variety of common audio players, but it can't be heard.

The persons having ordinary skill in the art can understand, the implementation of all or part of above mentioned embodiments, can be realized not only by hardware, but also through the computer program to instruction related hardware. The program can be stored in a computer readable storage medium, and can be executed to fulfill the function of above mentioned embodiments. Among them, the embodiment of the signal data acquisition unit 1 can be a computer file input device or data input interface, such as CD, USB interface, network interface, for obtaining data and sending data to data processing unit 2; data processing unit 2 can comprise computer CPU and memory, being used to complete signal mapping, normalization or to determine the strength of the output audio signal, and to save the audio file; audio play device 3 can be computer built-in audio player, being used for D/A converting the audio data from the data processing unit 2 and playing D/A converting results. The audio files generated by the data processing unit 2 can be stored in computer memory and hard drive, and can be output through the network interface or USB interface.

The above mentioned are only part of the embodiments of the invention, not all of the embodiments. All the other embodiments that a skilled person in this field may obtained without creative work, are belong to the protection scope of this invention.

INDUSTRIAL APPLICABILITY

Disclosed in the present invention are a method and an apparatus for auscultating inaudible signals, and thus inaudible signals can be mapped into the audible range to form audible signals. The method and apparatus make full use of general signal data acquisition unit and audio play device, reducing the cost of the invention implementation, and thus is easy to promote; by means of the method and apparatus of the present invention, auscultation can be achieved on any physical parameter changes expressed by wave-shaped curve, which promises to extract information which would have been difficult to find within the inaudible signal in the prior art and promote the development of science and technology innovations.

The invention claimed is:

1. A method for auscultating non-sound signals, wherein the method comprises:
    obtaining non-sound data, wherein the non-sound data represents physical parameter changes configured to be expressed in a waveform format;
    processing the non-sound data, wherein processing the non-sound data includes extracting a waveform from the non-sound data and normalizing the extracted waveform;
    mapping the normalized waveform into an audible signal, wherein mapping the normalized waveform includes combining the normalized waveform with an audible play rate to form the audible signal; and
    outputting the audible signal with an audio player device.

2. The method according to claim 1, wherein said extracting a waveform from the non-sound data includes ignoring parameters other than the waveform.

3. The method according to claim 1, wherein said normalizing the extracted waveform includes calculating maximum value and minimum value from the extracted waveform.

4. The method according to claim 1, wherein said normalizing the extracted waveform includes calculating all acquired signals to find out a signal with maximum amplitude variation, and calculating maximum and minimum value of the signal, and the maximum and minimum value of the signal are used for normalizing all acquired signals.

5. The method according to claim 1, wherein said combining the normalized waveform with an audible play rate to form an audible signal, further comprises:
    saving the audible signal in audio file format capable of being played by an audio player.

6. The method according to claim 1, wherein the non-sound data includes statistical results of a physical phenomenon.

7. The method according to claim 1, wherein the non-sound data includes voltage change of an electronic circuit.

8. The method according to claim 1, wherein said processing the non-sound data includes: extracting multiple waveforms from multiple data, and combining the waveforms with an audible play rate to form a multichannel audible signal.

9. An apparatus for auscultating non-sound signals, comprising:
a signal data acquisition unit configured to obtain non-sound data, wherein the signal data acquisition unit includes an analog-to-digital sampling unit and the non-sound data represents physical parameter changes configured to be expressed in a waveform format;
a signal processing unit configured to process non-sound data and map a processed waveform into an audible signal, wherein the signal processing unit includes a calculation unit and storage unit; and
an audio play device configured to output the audible signal, wherein the audio play device includes a digital-to-analog conversion unit and an electric-to-acoustic conversion unit;
wherein processing the non-sound data includes extracting a waveform from the non-sound data and normalizing the extracted waveform, and mapping the processed waveform includes combining the normalized waveform with an audible play rate to form the audible signal.

10. The apparatus according to claim 9, wherein the signal processing unit extracts the waveform from the data, including ignoring parameters other than the waveform.

11. The apparatus according to claim 9, wherein normalizing the extracted waveform includes calculating maximum value and minimum value from the extracted waveform.

12. The apparatus according to claim 9, wherein normalizing the extracted waveform includes calculating all acquired signals to find out a signal with maximum amplitude variation, and calculating maximum and minimum value of the signal, and the maximum and minimum value of the signal are used for normalizing all acquired signals.

13. The apparatus according to claim 9, wherein the non-sound data includes statistical results of a physical phenomenon, the statistical results of the physical phenomenon are mapped into audible signal by the signal processing unit.

14. The apparatus according to claim 9, wherein the non-sound data includes voltage change of an electronic circuit, the voltage change is mapped into audible signal by the signal processing unit.

15. The apparatus according to claim 9, wherein the signal processing unit combining the normalized waveform with an audible play rate to form an audible signal, further comprises:
saving the audible signal in audio file format capable of being played by an audio player.

16. The apparatus according to claim 9, wherein the signal processing unit also extracts multiple waveforms from multiple data, and combines the waveforms with an audible play rate to form a multichannel audible signal.

17. The apparatus according to claim 9, wherein the signal processing unit extracts waveform from data, and combines the waveform with a play rate which makes the waveform inaudible through an audio play apparatus, to thereby constitute an inaudible signal.

* * * * *